(12) United States Patent
Marsh et al.

(10) Patent No.: US 10,973,744 B2
(45) Date of Patent: *Apr. 13, 2021

(54) CONDITIONER COMPOSITION COMPRISING A CHELANT

(71) Applicant: The Procter & Gamble Company, Cincinnati, OH (US)

(72) Inventors: Jennifer Mary Marsh, Deerfield Township, OH (US); Casey Patrick Kelly, Wyoming, OH (US); Mark Robert Sivik, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/985,902

(22) Filed: Aug. 5, 2020

(65) Prior Publication Data

US 2020/0360254 A1 Nov. 19, 2020

Related U.S. Application Data

(63) Continuation of application No. 15/630,431, filed on Jun. 22, 2017, now abandoned.

(60) Provisional application No. 62/356,976, filed on Jun. 30, 2016.

(51) Int. Cl.
| | |
|---|---|
| *A61K 8/41* | (2006.01) |
| *A61Q 5/12* | (2006.01) |
| *A61K 8/34* | (2006.01) |
| *A61K 8/46* | (2006.01) |
| *A61K 8/49* | (2006.01) |
| *A61K 8/891* | (2006.01) |
| *A61K 8/898* | (2006.01) |
| *A61Q 5/00* | (2006.01) |

(52) U.S. Cl.
CPC ............... *A61K 8/41* (2013.01); *A61K 8/342* (2013.01); *A61K 8/416* (2013.01); *A61K 8/463* (2013.01); *A61K 8/49* (2013.01); *A61K 8/891* (2013.01); *A61K 8/898* (2013.01); *A61Q 5/002* (2013.01); *A61Q 5/12* (2013.01); *A61K 2800/51* (2013.01)

(58) Field of Classification Search
None
See application file for complete search history.

(56) References Cited

U.S. PATENT DOCUMENTS

| | | |
|---|---|---|
| 3,940,482 A | 2/1976 | Grand |
| 4,089,945 A | 5/1978 | Brinkman et al. |
| 4,185,106 A | 1/1980 | Dittmar et al. |
| 4,321,156 A | 3/1982 | Bushman |
| 4,412,943 A | 11/1983 | Hirota et al. |
| 4,749,507 A | 6/1988 | Varco |
| 4,822,604 A | 4/1989 | Knoll et al. |
| 4,855,130 A | 8/1989 | Konrad et al. |
| 5,306,489 A | 4/1994 | Goldberg et al. |
| 5,559,092 A | 9/1996 | Gibson et al. |
| 5,635,167 A | 6/1997 | Said et al. |
| 5,804,172 A | 9/1998 | Ault |
| 5,847,003 A | 12/1998 | Ptchelintsev et al. |
| 6,069,169 A | 5/2000 | Ptchelintsev et al. |
| 6,071,962 A | 6/2000 | Ptchelintsev et al. |
| 6,287,547 B1 | 9/2001 | Oota et al. |
| 6,348,189 B1 | 2/2002 | Tanabe et al. |
| 6,358,502 B1 | 3/2002 | Tanabe et al. |
| 6,365,143 B1 | 4/2002 | Lundmark et al. |
| 6,380,263 B1 | 4/2002 | Pruche et al. |
| 6,432,147 B1 | 8/2002 | Dias et al. |
| 6,432,394 B2 | 8/2002 | Pyles et al. |
| 6,509,011 B1 | 1/2003 | Ellis et al. |
| 6,544,500 B1 | 4/2003 | O'Toole et al. |
| 6,551,361 B1 | 4/2003 | Cornwell et al. |
| 6,602,493 B2 | 8/2003 | Akhter et al. |
| 6,624,126 B1 | 9/2003 | Kasuga et al. |
| 6,743,434 B1 | 6/2004 | Lundmark et al. |
| 6,858,202 B2 | 2/2005 | Niemiec et al. |
| 6,864,314 B1 | 3/2005 | Yeung et al. |
| 6,927,196 B2 | 8/2005 | Snyder et al. |
| 7,045,493 B2 | 5/2006 | Wang et al. |
| 7,169,743 B2 | 1/2007 | Wang et al. |
| 7,186,274 B2 | 3/2007 | Vic et al. |
| 7,186,275 B2 | 3/2007 | Boswell |
| 7,300,647 B1 | 11/2007 | O'Toole et al. |
| 7,335,700 B2 | 2/2008 | Yeung et al. |
| 7,547,454 B2 | 6/2009 | Gupta |
| 7,700,078 B2 | 4/2010 | Huglin et al. |
| 7,709,430 B2 | 5/2010 | Mizushima |
| 7,745,382 B2 | 6/2010 | Sloan |

(Continued)

FOREIGN PATENT DOCUMENTS

| | | |
|---|---|---|
| CA | 1147262 A | 5/1983 |
| DE | 19536420 A1 | 4/1996 |

(Continued)

OTHER PUBLICATIONS

Alberto Culver, Canada, Shampoo, Mintel GNPD, Mar. 2008.
All final and non-final office actions for U.S. Appl. No. 13/737,035.
All final and non-final office actions for U.S. Appl. No. 13/920,171.
All final and non-final office actions for U.S. Appl. No. 15/630,411.
All final and non-final office actions for U.S. Appl. No. 15/630,426.
All final and non-final office actions for U.S. Appl. No. 15/630,431.

(Continued)

*Primary Examiner* — David J Blanchard
*Assistant Examiner* — Sarah J Chickos
(74) *Attorney, Agent, or Firm* — Alexandra S. Anoff

(57) ABSTRACT

Described herein is a hair conditioner composition and methods of using the same, the hair conditioner composition including an effective chelant. The hair conditioner composition further includes one or more high melting point fatty compounds and a cationic surfactant.

19 Claims, No Drawings

(56) References Cited

U.S. PATENT DOCUMENTS

| | | |
|---|---|---|
| 7,915,212 B2 | 3/2011 | Yeung et al. |
| 8,022,020 B2 | 9/2011 | Sloan |
| 8,039,424 B2 | 10/2011 | Sloan |
| 8,404,257 B1 | 3/2013 | Huglin et al. |
| 8,449,868 B2 | 5/2013 | Jennings et al. |
| 8,637,489 B2 | 1/2014 | Van Nguyen et al. |
| 8,942,481 B2 | 1/2015 | Suarez Cambre et al. |
| 9,044,413 B2 | 6/2015 | Yeung et al. |
| 9,080,135 B2 | 7/2015 | Hough et al. |
| 9,271,908 B2 | 3/2016 | Allef et al. |
| 9,358,195 B2 | 6/2016 | Lupia et al. |
| 9,586,063 B2 | 3/2017 | Marsh et al. |
| 9,642,788 B2 | 5/2017 | Marsh et al. |
| 10,539,872 B2 | 1/2020 | Tadokoro |
| 2003/0095938 A1 | 5/2003 | Casero |
| 2003/0125224 A1 | 7/2003 | Seitz, Jr. et al. |
| 2003/0176303 A1 | 9/2003 | Niemiec et al. |
| 2003/0211953 A1 | 11/2003 | Glenn et al. |
| 2003/0215522 A1 | 11/2003 | Johnson et al. |
| 2004/0058855 A1 | 3/2004 | Schwartz et al. |
| 2004/0123402 A1 | 7/2004 | Marsh et al. |
| 2004/0261198 A1 | 12/2004 | Kainz et al. |
| 2004/0266656 A1 | 12/2004 | Sakurai |
| 2005/0095215 A1 | 5/2005 | Popp |
| 2005/0095261 A1 | 5/2005 | Popp |
| 2005/0239723 A1 | 10/2005 | Amin |
| 2005/0256313 A1 | 11/2005 | Norenberg et al. |
| 2006/0009371 A1 | 1/2006 | Wang et al. |
| 2006/0063695 A1 | 3/2006 | Wang et al. |
| 2006/0130246 A1 | 6/2006 | Molenda et al. |
| 2008/0057015 A1 | 3/2008 | Oblong et al. |
| 2008/0145328 A1 | 6/2008 | Schwartz |
| 2009/0074700 A1 | 3/2009 | Nguyen et al. |
| 2009/0092561 A1 | 4/2009 | Lupia et al. |
| 2010/0069338 A1 | 3/2010 | Ward et al. |
| 2010/0195039 A1 | 8/2010 | Park |
| 2011/0015120 A1 | 1/2011 | Bortolin |
| 2012/0034181 A1 | 2/2012 | Hoffmann et al. |
| 2012/0034182 A1 | 2/2012 | Hoffmann et al. |
| 2013/0122070 A1* | 5/2013 | Barnett .................. A61Q 19/10 424/401 |
| 2013/0174863 A1 | 7/2013 | Marsh et al. |
| 2013/0333715 A1 | 12/2013 | Hutton, III et al. |
| 2014/0079660 A1 | 3/2014 | Doi |
| 2014/0213499 A1* | 7/2014 | Chen .................. A61Q 5/02 510/321 |
| 2015/0011449 A1 | 1/2015 | Snyder et al. |
| 2015/0030644 A1 | 1/2015 | Oh et al. |
| 2015/0093420 A1* | 4/2015 | Snyder .................. A61K 8/416 424/401 |
| 2015/0140052 A1 | 5/2015 | Gizaw |
| 2015/0182431 A1 | 7/2015 | Chaudhuri |
| 2016/0175210 A1 | 6/2016 | Marsh et al. |
| 2018/0000705 A1 | 1/2018 | Marsh |
| 2018/0000706 A1 | 1/2018 | Marsh |
| 2018/0000713 A1 | 1/2018 | Marsh |
| 2018/0000714 A1 | 1/2018 | Marsh |
| 2018/0000715 A1 | 1/2018 | Marsh |
| 2019/0336426 A1 | 11/2019 | Marsh |

FOREIGN PATENT DOCUMENTS

| | | |
|---|---|---|
| DE | 10259199 A1 | 6/2004 |
| DE | 102011079664 A1 | 4/2012 |
| EP | 1046390 A1 | 10/2000 |
| EP | 1714634 A1 | 10/2006 |
| EP | 2067467 A2 | 6/2009 |
| FR | 2853529 A1 | 10/2004 |
| FR | 2853530 A1 | 10/2004 |
| FR | 2853531 A1 | 10/2004 |
| GB | 2288812 A | 1/1995 |
| GB | 2315770 A | 2/1998 |
| JP | S57109711 A | 7/1982 |
| JP | S63150213 A | 6/1988 |
| JP | 05262623 | 10/1993 |
| JP | 06041579 | 2/1994 |
| JP | H07258698 A | 10/1995 |
| JP | H09183996 A | 7/1997 |
| JP | H09291024 A | 11/1997 |
| JP | H11139941 A | 5/1999 |
| JP | 11180836 A | 7/1999 |
| JP | 11269487 | 10/1999 |
| JP | 2004059540 | 2/2004 |
| JP | 2006160708 A | 6/2006 |
| JP | 2008169183 | 7/2008 |
| JP | 2011046652 | 3/2011 |
| KR | 1020090077562 A | 7/2009 |
| WO | WO9116878 A1 | 11/1991 |
| WO | WO9311737 A1 | 6/1993 |
| WO | WO9804237 A1 | 2/1998 |
| WO | WO9824400 A2 | 6/1998 |
| WO | WO0051555 A1 | 9/2000 |
| WO | WO0051556 A1 | 9/2000 |
| WO | WO200119327 A1 | 3/2001 |
| WO | WO0220486 A2 | 3/2002 |
| WO | WO02065982 A2 | 8/2002 |
| WO | WO02102302 A2 | 12/2002 |
| WO | WO2007079793 A1 | 7/2007 |
| WO | WO2008136000 A2 | 11/2008 |
| WO | WO2008153050 A1 | 12/2008 |
| WO | WO2010106342 A2 | 9/2010 |
| WO | WO201220226 A1 | 2/2012 |
| WO | WO2012021472 A1 | 2/2012 |
| WO | WO2014182766 A1 | 11/2014 |

OTHER PUBLICATIONS

All final and non-final office actions for U.S. Appl. No. 15/630,437.
All final and non-final office actions for U.S. Appl. No. 15/630,899.
All final and non-final office actions for U.S. Appl. No. 16/515,821.
Gary W. Evans, "The Role of Picolinic acid in Metal Metabolism", Life Chemistry Reports, Jan. 1, 1982, pp. 57-67.
PCT International Search Report and Written Opinion for PCT/US2013/020735 dated Aug. 5, 2013.
PCT International Search Report and Written Opinion for PCT/US2017/038897 dated Sep. 18, 2017.
PCT International Search Report and Written Opinion for PCT/US2017/038899 dated Aug. 21, 2017.
PCT International Search Report and Written Opinion for PCT/US2017/038900 dated Aug. 21, 2017.
PCT International Search Report and Written Opinion for PCT/US2017/038903 dated Sep. 25, 2017.
PCT International Search Report and Written Opinion for PCT/US2017/038904 dated Sep. 18, 2017.
Procter & Gamble, UK, 0% Grease Shampoo, Mintel, Feb. 2016.
Vitality Unlimited: "What's a Picolinate?—Picolinic acid is the body's prime natural chelator", Dec. 30, 1989.
Zurowska Bogum Ed—Lippert Bernhard et al, "Structural and Magnetic characterization of Cu-picolinate and Cu-Quinaldinate nad their mixed complexes with water or halides", Inorganica Chimica Acta, vol. 418, May 2, 2014, pp. 136-152.
U.S. Appl. No. 16/931,880, filed Jul. 20, 2020, Marsh et al.

* cited by examiner

CONDITIONER COMPOSITION COMPRISING A CHELANT

FIELD OF THE INVENTION

Described herein are hair conditioner compositions comprising one or more chelants, one or more high melting point fatty compounds, a cationic surfactant, and a carrier. The hair conditioner composition inhibits both deposition/penetration of copper salts and other transition metal salts in the hair and removes such salts from hair fiber. A method of treating hair with the hair conditioner composition is also described herein.

BACKGROUND OF THE INVENTION

Many water sources that are used by consumers for personal care contain elevated levels of calcium and magnesium salts, as well as undesirable levels of redox metals (e.g., copper and/or iron) salts. As such, using chelants to sequester trace redox metals often proves to be ineffective because most chelants also competitively bind calcium and/or magnesium.

It has been found that even trace quantities of these minerals can deposit on the hair surface and in between the cuticle layers of hair. This deposition of minerals on hair is especially problematic because transition metal ions, such as copper and iron, can facilitate reduction-oxidation (redox) reactions during hair coloring treatments and during UV exposure. These reactions generate reactive oxygen species (ROS), which in turn can cause damage to the hair. In addition, they can interfere with the oxidative color formation chemistry and lead to reduced color uptake for hair colorant users.

It has also been found that traditional chelating agents such as EDDS can result in stability problems for conditioners containing cationic surfactants.

Accordingly, there is a need for hair care compositions that can inhibit minerals depositing on keratinous tissue, as well as facilitate the removal of minerals already deposited thereon. Additionally, there is a need for chelating agents which can facilitate removal of minerals deposited on the hair without interfering with the hair care formulation in which the chelating agent is included.

SUMMARY OF THE INVENTION

Described herein is a hair conditioner composition comprising:
(a) from about 0.005% to about 5% of one or more chelants, by weight of the hair conditioner composition, wherein the one or more chelants have a molecular structure as follows:

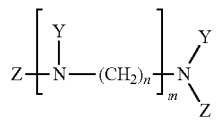

wherein n is 2 or 3; m is 1, 2, 3, or 4; and
Y and Z are independently selected from the group consisting of hydrogen, methyl, ethyl, propyl, butyl, pentyl, —CH$_2$CH$_2$OH, —CH$_2$CH(CH$_3$)OH), —CH$_2$CH$_2$NH$_2$, —CH$_2$CH(CH$_3$) NH$_2$, and combinations thereof;

and wherein the one or more chelants comprise:
(1) log of the formation constant logK$_{ML}$ of its complex with copper is higher than 6;
(2) log P value is from about −5 to about 2; and
(3) molecular weight of from about 50 to about 500;
(b) from about 0.1% to about 20% of one or more high melting point fatty compounds, by weight of the hair conditioner composition;
(c) from about 0.1% to about 10% of a cationic surfactant, by weight of the hair conditioner composition; and
(d) from about 75% to about 98% of an aqueous carrier, by weight of the hair conditioner composition;
wherein the hair conditioner composition has a pH from about 3 to about 8.

DETAILED DESCRIPTION OF THE INVENTION

While the specification concludes with claims particularly pointing out and distinctly claiming the invention, it is believed that the hair conditioner composition described herein will be better understood from the following description.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein. As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. Unless otherwise noted, all such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. "QS" means sufficient quantity for 100%.

As used herein, the term "fluid" includes liquids and gels.

As used herein, the term "log x" refers to the common (or decadic) logarithm of x.

As used herein, the articles including "a" and "an" when used in a claim, are understood to mean one or more of what is claimed or described.

As used herein, "mixtures" is meant to include a simple combination of materials and any compounds that may result from their combination.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights percents (wt %) as they pertain to listed ingredients are based on the active level and do not include carriers or by-products that may be included in commercially available materials, unless otherwise specified.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, and/or alcohol derivatives of a given compound.

"Polymer," as used herein, means a chemical formed from the polymerisation of two or more monomers, which may be the same or different. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The term log P is the n-octanol/water partition coefficients of the material. All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Conditioner Composition

The hair composition described herein is a conditioning hair care composition that delivers consumer desired conditioning in addition to inhibiting the deposition of minerals (i.e. from the water used to rinse) on the hair. The hair conditioner composition comprises: (a) from about 0.005% to about 5% of one or more chelants, by weight of the hair conditioner composition; (b) from about 0.1% to about 20% of one or more high melting point fatty compounds, by weight of the hair conditioner composition; (c) from about 0.1% to about 10% of a cationic surfactant, by weight of the hair conditioner composition; and (d) from about 75% to about 98% of an aqueous carrier, by weight of the hair conditioner composition; wherein the hair conditioner composition has a pH from about 3 to about 8.

A. Chelants

The hair conditioner composition comprises from about 0.005% to about 10%, alternatively from about 0.01% to about 5%, alternatively from about 0.05% to about 3%, alternatively from about 0.1% to about 1.5%, and alternatively from about 0.1% to about 0.5% of one or more chelants, by weight of the hair conditioner composition, wherein the one or more chelants have a molecular structure as follows:

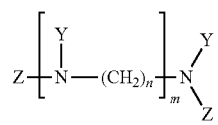

wherein n is 2 or 3; m is 1, 2, 3, or 4; and

Y and Z are independently selected from the group consisting of hydrogen, methyl, ethyl, propyl, butyl, pentyl, —$CH_2CH_2OH$, —$CH_2CH(CH_3)OH$), —$CH_2CH_2NH_2$, —$CH_2CH(CH_3)NH_2$, and combinations thereof;

and wherein the one or more chelants comprise:
(1) log of the formation constant $logK_{ML}$ of its complex with copper is higher than 6;
(2) log P value is from about −5 to about 2; and
(3) molecular weight of from about 50 to about 500.

Stability Constants of Exemplary Chelants

The relative affinity of a chelant at a specified pH for $Cu^{+2}$ can be assessed by its Stability Constant. The Stability Constant of a metal chelant interaction is defined as:

$$K_{ML} = \frac{[ML]}{[M][L]}$$

where:
[ML] is the concentration of metal ligand complex at equilibrium;
[M] is the concentration of free metal ion;
[L] is the concentration of free ligand in a fully deprotonated form; and
$K_{ML}$ is the stability constant for the metal chelant complex.

The stability constants of chelant-metal ion complexes are well documented in the literature for commonly used chelants (see, for example, Arthur Martell & Robert M Smith, Critically Selected Stability Constants of Metal Complexes Database, Version 3.0 and above, incorporated herein by reference). When not documented the constants can be measured using various analytical methods (see "Metal Complexes in Aqueous Solutions", Martel and Hancock, edition Modem Inorganic Chemistry, p. 226-228, incorporated herein by reference).

It has been found that effective chelants need to have a high affinity for copper in order to preferentially bind copper found in hair. However, it has been found that also important to efficacy is the ability for the chelant to penetrate inside the hair fibers rapidly during the shampoo lathering process (which typically lasts between 30 seconds and 1 minute).

The copper to be removed is inside the hair and the chelant needs to penetrate inside hair and form a strong copper-chelant complex. This copper-chelant complex needs to be water soluble and thus easily removed during the rinsing process. To be able to do this, two additional parameters have been shown to be important for chelant efficacy. These are log P, the octanol/water partitioning coefficient, and the molecular weight of the chelant. Both are related to the ability of the chelant to penetrate into hair and also form a water soluble copper-chelant complex The one or more chelants for use in the shampoo composition may be selected from the group consisting of triethylenetetramine, tetraethylenepenatmine, pentaethylenehexamine, tris(2-aminoethyl)amine, ethylenedinitrilotetrapropan-2-ol, 1,1',1"-[[2-hydroxypropyl)imino]bis(2,1-ethanediylnitrilo)]tetrakis-2-propanol, tetraethylenepentaamine-(1-EO), 1,5,9,13-tetraazatridecane, and mixtures thereof.

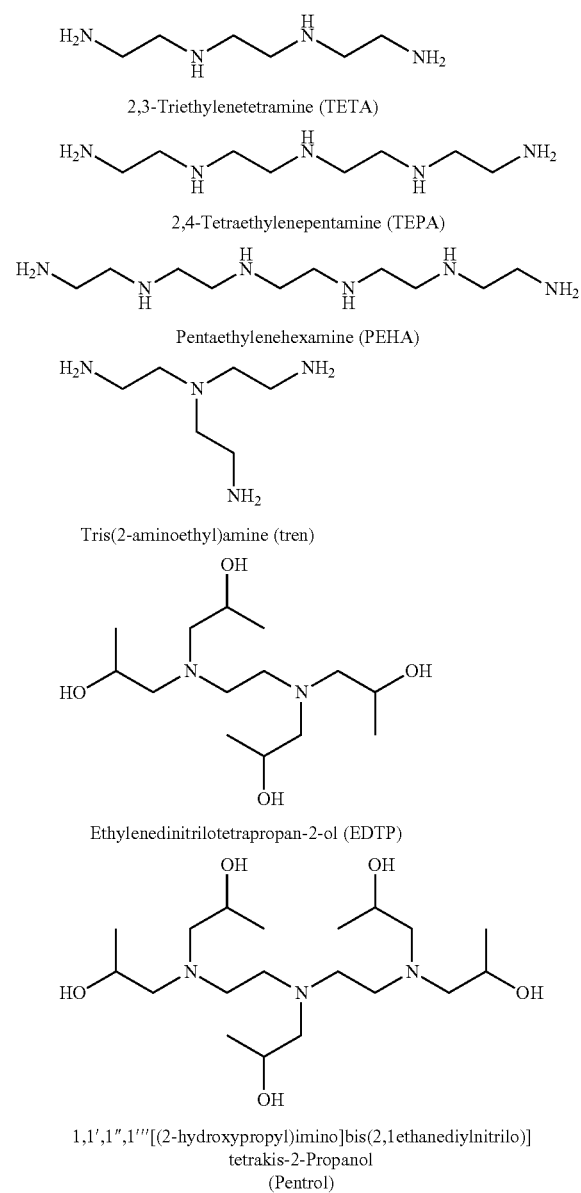

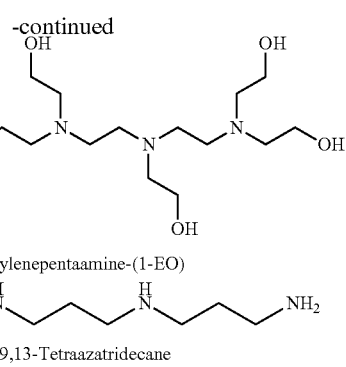

Tetraethylenepentaamine-(1-EO)

1,5,9,13-Tetraazatridecane

The log of the formation constant $logK_{ML}$ of its complex with copper can be higher than 6, alternatively higher than 8, alternatively higher than 9, alternatively higher than 10, alternatively higher than 12, alternatively higher than 14, alternatively higher than 16, alternatively higher than 17, alternatively higher than 18, and alternatively higher than 20. The log of the formation constant logKAiL of its complex with copper can be from about 6 to about 28, alternatively from about 8 to about 27, alternatively from about 9 to about 26, alternatively from about 10 to about 25, alternatively from about 12 to about 24, alternatively from about 14 to about 24, alternatively from about 16 to about 24, alternatively from about 17 to about 24, alternatively from about 18 to about 24, and alternatively from about 20 to about 23.

The log P value of the one or more chelants can be from about −5 to about 2, alternatively from about −4 to about 1, alternatively from about −3.5 to about 0, and alternatively from about −2.9 to about −2.5.

The molecular weight of the one or more chelants can be from about 50 to about 500, alternatively from about 75 to about 400, alternatively from about 100 to about 350, alternatively from about 125 to about 325, alternatively from about 140 to about 300, alternatively from about 140 to about 200.

Other chelants that can be used to reduce copper content of hair have the following general structure:

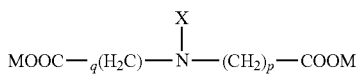

wherein M is hydrogen or a metal ion;
p is 1 or 2;
q is 1 or 2; and
X is selected from the group containing hydrogen, methyl, ethyl, propyl, —CH$_2$CH$_2$OH, —CH$_2$CH(CH$_3$)OH), —CH$_2$CH$_2$NH$_2$, —CH$_2$CH(CH$_3$) NH$_2$, —CH$_2$COOM, or —CH$_2$CH$_2$SH, and —CH$_2$CH(CH$_3$)SH).

Non-limiting examples of the one or more chelants include iminodiacetic acid, N-(2-hydroxyethyl)iminodiacetic acid, N-methyliminodiacetic acid, N-(2-aminoethyl)iminodiacetic acid, N-propyliminodiacetic acid, and nitrilotriacetic acid.

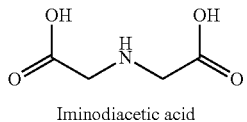

Iminodiacetic acid

-continued

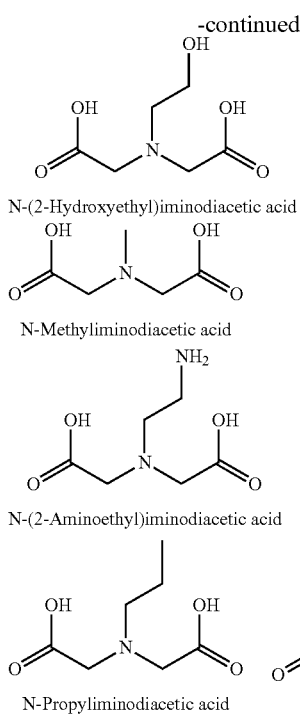

N-(2-Hydroxyethyl)iminodiacetic acid

N-Methyliminodiacetic acid

N-(2-Aminoethyl)iminodiacetic acid

N-Propyliminodiacetic acid

Nitrilotriacetic acid

B. Cationic Surfactant System

The hair care composition described herein comprises a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the hair conditioner composition at a level of from about 0.1% to about 10%, alternatively from about 0.5% to about 8%, alternatively from about 0.8% to about 5%, and alternatively from about 1.0% to about 4%, by weight of the hair conditioner composition.

Mono-Long Alkyl Quaternized Ammonium Salt

The monoalkyl quaternized ammonium salt cationic surfactants useful herein are those having one long alkyl chain which has from 12 to 30 carbon atoms, from 16 to 24 carbon atoms, and in one embodiment at C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

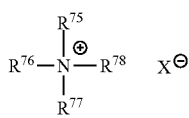

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, from 16 to 24 carbon atoms, from 18 to 22 carbon atoms, an/or 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as $\ell$-glutamic acid, lactic acid, hydrochloric acid, malic acid, succinic acid, acetic acid, fumaric acid, tartaric acid, citric acid, $\ell$-glutamic hydrochloride, maleic acid, and mixtures thereof; in one embodiment $\ell$-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The dialkyl quaternized ammonium salt cationic surfactants useful herein are those having two long alkyl chains having 12-30 carbon atoms, and/or 16-24 carbon atoms, and/or 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, from 16 to 24 carbon atoms, from 18 to 22 carbon atoms, and/or 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

C. High Melting Point Fatty Compound

The hair conditioner composition comprises one or more high melting point fatty compounds. The one or more high melting point fatty compounds useful herein can have a melting point of 25° C. or higher, and can be selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the hair conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The one or more high melting point fatty compounds can be included in the hair care composition at a level of from about 0.1% to about 20%, alternatively from about 1% to about 15%, and alternatively from about 1.5% to about 8%, by weight of the hair conditioner. The one or more high melting point fatty compounds can provide improved conditioning benefits such as slippery feel during the application of the hair conditioner composition to wet hair, hair softness on dry hair, and moisturized feel on dry hair.

D. Aqueous Carrier

The hair care composition comprises an aqueous carrier at a level of from about 75% to about 98%, alternatively from about 80% to about 95%, by weight of the hair care composition. Accordingly, the hair care composition can be in the form of pourable liquids (under ambient conditions). The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier can include water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The hair conditioner composition may have a pH in the range from about 2 to about 10, alternatively from about 3 to about 8, at 25° C. The hair care composition can also be effective toward washing out the existing minerals and redox metals deposits, which can reduce cuticle distortion and thereby reduce cuticle chipping and damage.

E. Gel Matrix

The hair conditioner composition can comprise a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, and/or from about 1:1 to about 1:6.

F. Additional Components

1. Silicone Conditioning Agent

The hair conditioner composition can include a silicone conditioning agent which comprises a silicone compound. The silicone compound may comprise volatile silicone, non-volatile silicones, or combinations thereof. If volatile silicones are present, it will typically be incidental to their use as a solvent or carrier for commercially available forms of non-volatile silicone materials ingredients, such as silicone gums and resins. The silicone compounds may comprise a silicone fluid conditioning agent and may also comprise other ingredients, such as a silicone resin to improve silicone fluid deposition efficiency or enhance glossiness of the hair. The concentration of the silicone compound in the hair conditioner composition typically ranges from about 0.01 wt % to about 10 wt %, from about 0.1 wt % to about 8 wt %, from about 0.1 wt % to about 5 wt %, or even from about 0.2 wt % to about 3 wt %.

Exemplary silicone compounds include (a) a first polysiloxane which is non-volatile, substantially free of amino groups, and has a viscosity of from about 100,000 $mm^2s^{-1}$ to about 30,000,000 $mm^2s^{-1}$; (b) a second polysiloxane which is non-volatile, substantially free of amino groups, and has a viscosity of from about 5 $mm^2s^{-1}$ to about 10,000 $mm^2s^{-1}$; (c) an aminosilicone having less than about 0.5 wt % nitrogen by weight of the aminosilicone; (d) a silicone copolymer emulsion with an internal phase viscosity of greater than about $100\times10^6$ $mm^2s^{-1}$, as measured at 25° C.; (e) a silicone polymer containing quaternary groups; or (1) a grafted silicone polyol, wherein the silicone compounds (a)-(f) are disclosed in U.S. Patent Application Publication Nos. 2008/0292574, 2007/0041929, 2008/0292575, and 2007/0286837, each of which is incorporated by reference herein in its entirety.

a. First Polysiloxane

The hair conditioner composition may comprise a first polysiloxane. The first polysiloxane is non-volatile, and substantially free of amino groups. The first polysiloxanes being "substantially free of amino groups" can mean that the first polysiloxane contains 0 wt % of amino groups. The first polysiloxane has a viscosity of from about 100,000 $mm^2s^{-1}$ to about 30,000,000 $mm^2s^{-1}$ at 25° C. For example, the viscosity may range from about 300,000 $mm^2s^{-1}$ to about 25,000,000 $mm^2s^{-1}$, or from about 10,000,000 $mm^2s^{-1}$ to about 20,000,000 $mm^2s^{-1}$. The first polysiloxane has a molecular weight from about 100,000 to about 1,000,000. For example, the molecular weight may range from about 130,000 to about 800,000, or from about 230,000 to about 600,000. According to one aspect, the first polysiloxane may be nonionic.

Exemplary first non-volatile polysiloxanes useful herein include those in accordance with the following the general formula (I):

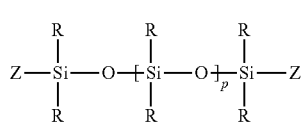
(I)

wherein R is alkyl or aryl, and p is an integer from about 1,300 to about 15,000, such as from about 1,700 to about 11,000, or from about 3,000 to about 8,000. Z represents groups which block the ends of the silicone chains. The alkyl or aryl groups substituted on the siloxane chain (R) or at the ends of the siloxane chains Z can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. According to an embodiment, suitable Z groups include hydroxy, methyl, methoxy, ethoxy, propoxy, and aryloxy. The two R groups on each silicon atom may represent the same group or different groups. According to one embodiment, the two R groups may represent the same group. Suitable R groups include methyl, ethyl, propyl, phenyl, methylphenyl and phenylmethyl. Exemplary silicone compounds include polydimethylsiloxane, polydiethylsiloxane, and polymethylphenylsiloxane. According to one embodiment, polydimethylsiloxane is the first polysiloxane. Commercially available silicone compounds useful herein include, for example, those available from the General Electric Company in their TSF451 series, and those available from Dow Corning in their Dow Corning SH200 series.

The silicone compounds that can be used herein also include a silicone gum. The term "silicone gum", as used herein, means a polyorganosiloxane material having a viscosity at 25° C. of greater than or equal to 1,000,000 $mm^2s^{-1}$. It is recognized that the silicone gums described herein can also have some overlap with the above-disclosed silicone compounds. This overlap is not intended as a limitation on any of these materials. The "silicone gums" will typically have a mass molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A available from the General Electric Company.

b. Second Polysiloxane

The hair conditioner composition may comprise a second polysiloxane. The second polysiloxane is non-volatile, and substantially free of amino groups. In the present invention, the second polysiloxane being "substantially free of amino groups" means that the second polysiloxane contains 0 wt % of amino groups. The second polysiloxane has a viscosity of from about 5 $mm^2s^{-1}$ to about 10,000 $mm^2s^{-1}$ at 25° C., such as from about 5 $mm^2s^{-1}$ to about 5,000 $mm^2s^{-1}$, from about 10 $mm^2s^{-1}$ to about 1,000 $mm^2s^{-1}$, or from about 20 $mm^2s^{-1}$ to about 350 $mm^2s^{-1}$. The second polysiloxane has a molecular weight of from about 400 to about 65,000. For example, the molecular weight of the second polysiloxane may range from about 800 to about 50,000, from about 400 to about 30,000, or from about 400 to about 15,000. According to one aspect, the second polysiloxane may be nonionic. According to another aspect, the second polysiloxane may be a linear silicone.

Exemplary second non-volatile polysiloxanes useful herein include polyalkyl or polyaryl siloxanes in accordance with the following the general formula (II):

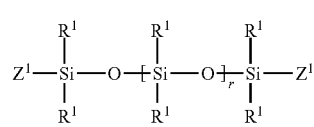
(II)

wherein $R^1$ is alkyl or aryl, and r is an integer from about 7 to about 850, such as from about 7 to about 665, from about 7 to about 400, or from about 7 to about 200. $Z^1$ represents groups which block the ends of the silicone chains. The alkyl or aryl groups substituted on the siloxane chain (R') or at the ends of the siloxane chains $Z^1$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. According to an embodiment, suitable $Z^1$ groups include hydroxy, methyl, methoxy, ethoxy, propoxy, and aryloxy. The two $R^1$ groups on each silicon atom may represent the same group or different groups. According to one embodiment, the two $R^1$ groups may represent the same group. Suitable $R^1$ groups include methyl, ethyl, propyl, phenyl, methylphenyl and phenylmethyl. Exemplary silicone compounds include polydimethylsiloxane, polydiethylsiloxane, and polymethylphenylsiloxane. According to one embodiment, polydimethylsiloxane is the second polysiloxane. Commercially available silicone compounds useful herein include, for example, those available from the General Electric Company in their TSF451 series, and those available from Dow Corning in their Dow Corning SH200 series.

c. Aminosilicone

The hair conditioner composition may comprise an amino silicone having less than about 0.5 wt % nitrogen by weight of the aminosilicone, such as less than about 0.2 wt %, or less than about 0.1 wt %, in view of friction reduction benefit. It has been surprisingly found that higher levels of nitrogen (amine functional groups) in the amino silicone tend to result in less friction reduction, and consequently less conditioning benefit from the aminosilicone. The aminosilicone useful herein may have at least one silicone block with greater than 200 siloxane units, in view of friction reduction benefit. The aminosilicones useful herein include, for example, quaternized aminosilicone and non-quaternized aminosilicone.

In an embodiment, the aminosilicones useful herein are water-insoluble. "Water-insoluble aminosilicone" means that the aminosilicone has a solubility of 10 g or less per 100 g water at 25° C., in another embodiment 5 g or less per 100 g water at 25° C., and in another embodiment 1 g or less per 100 g water at 25° C. In the present invention, "water-insoluble aminosilicone" means that the aminosilicone is substantially free of copolyol groups. If copolyol groups are present, they are present at a level of less than 10 wt %, less than 1 wt %, or less than 0.1 wt % by weight of the aminosilicone.

Aminosilicones useful herein are those which conform to the general formula (III):

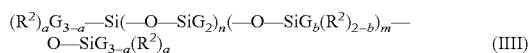

(IIII)

wherein G is hydrogen, phenyl, hydroxy, or $C_1$-$C_8$ alkyl, such as methyl; a is an integer having a value from 1 to 3, such as 1; b is an integer having a value from 0 to 2, such as 1; n is a number from 1 to 2,000, such as from 100 to 1,800, from 300 to 800, or from 500 to 600; m is an integer having a value from 0 to 1,999, such as from 0 to 10, or 0; $R^2$ is a monovalent radical conforming to the general formula $C_qH_{2q}L$, wherein q is an integer having a value from 2 to 8 and L is selected from the following groups: —N($R^3$)$_2$ CH$_2$—CH$_2$—N($R^3$$_2$)$_2$; —N($R^3$)$_2$; —N$^+$($R^3$)$_3$A$^-$; —N($R^3$) CH$_2$—CH$_2$—N$^+$R$^3$H$_2$A$^-$; wherein $R^3$ is hydrogen, phenyl, benzyl, or a saturated hydrocarbon radical, such as an alkyl radical from about $C_1$ to about $C_{20}$; A$^-$ is a halide ion. According to an embodiment, L is —N(CH$_3$)$_2$ or —NH$_2$. According to another embodiment, L is —NH$_2$.

The aminosilicone of the above formula is used at levels by weight of the composition of from about 0.1 wt % to about 5 wt %, alternatively from about 0.2 wt % to about 2 wt %, alternatively from about 0.2 wt % to about 1.0 wt %, and alternatively from about 0.3 wt % to about 0.8 wt %.

According to one embodiment, the aminosilicone may include those compounds corresponding to formula (III) wherein m=0; a=1; q=3; G=methyl; n is from about 1400 to about 1700, such as about 1600; and L is —N(CH$_3$)$_2$ or —NH$_2$, such as —NH$_2$. According to another embodiment, the aminosilicone may include those compounds corresponding to formula (III) wherein m=0; a=1; q=3; G=methyl; n is from about 400 to about 800, such as from about 500 to around 600; and L is L is —N(CH$_3$)$_2$ or —NH$_2$, such as —NH$_2$. Accordingly, the aforementioned aminosilicones can be called terminal aminosilicones, as one or both ends of the silicone chain are terminated by nitrogen containing group. Such terminal aminosilicones may provide improved friction reduction compared to graft aminosilicones.

Another example of an aminosilicone useful herein includes, for example, quaternized aminosilicone having a tradename KF8020 available from Shinetsu.

The above aminosilicones, when incorporated into the hair care composition, can be mixed with solvent having a lower viscosity. Such solvents include, for example, polar or non-polar, volatile or non-volatile oils. Such oils include, for example, silicone oils, hydrocarbons, and esters. Among such a variety of solvents, exemplary solvents include those selected from the group consisting of non-polar, volatile hydrocarbons, volatile cyclic silicones, non-volatile linear silicones, and mixtures thereof. The non-volatile linear silicones useful herein are those having a viscosity of from about 1 mm$^2$s$^{-1}$ to about 20,000 mm$^2$s$^{-1}$, such as from about 20 mm$^2$s$^{-1}$ to about 10,000 mm$^2$s$^{-1}$, at 25° C. According to one embodiment, the solvents are non-polar, volatile hydrocarbons, especially non-polar, volatile isoparaffins, in view of reducing the viscosity of the aminosilicones and providing improved hair conditioning benefits such as reduced friction on dry hair. Such mixtures may have a viscosity of from about 1,000 mPa·s to about 100,000 mPa·s, and alternatively from about 5,000 mPa·s to about 50,000 mPa·s.

d. Silicone Copolymer Emulsion

The hair conditioner composition may comprise a silicone copolymer emulsion with an internal phase viscosity of greater than about 100×10$^6$ mm$^2$s$^{-1}$. The silicone copolymer emulsion may be present in an amount of from about 0.1 wt % to about 15 wt %, alternatively from about 0.3 wt % to about 10 wt %, and alternatively about 0.5 wt % to about 5 wt %, by weight of the composition, in view of providing clean feel.

According to one embodiment, the silicone copolymer emulsion has a viscosity at 25° C. of greater than about 100×10$^6$ mm$^2$s$^{-1}$, alternatively greater than about 120×10$^6$ mm$^2$s$^{-1}$, and alternatively greater than about 150×10$^6$ mm$^2$s$^{-1}$. According to another embodiment, the silicone copolymer emulsion has a viscosity at 25° C. of less than about 1000×10$^6$ mm$^2$s$^{-1}$, alternatively less than about 500×10$^6$ mm$^2$s$^{-1}$, and alternatively less than about 300×10$^6$ mm$^2$s$^{-1}$. To measure the internal phase viscosity of the silicone copolymer emulsion, one may first break the polymer from the emulsion. By way of example, the following procedure can be used to break the polymer from the emulsion: 1) add 10 grams of an emulsion sample to 15 milliliters of isopropyl alcohol; 2) mix well with a spatula; 3) decant the isopropyl alcohol; 4) add 10 milliliters of acetone and knead polymer with spatula; 5) decant the acetone; 6) place polymer in an aluminum container and flatten/dry with a paper towel; and 7) dry for two hours in an 80° C. The polymer can then be tested using any known rheometer, such as, for example, a CarriMed, Haake, or Monsanto rheometer, which operates in the dynamic shear mode. The internal phase viscosity values can be obtained by recording the dynamic viscosity (n') at a 9.900*10 Hz frequency point. According to one embodiment, the average particle size of the emulsions is less than about 1 micron, such as less than about 0.7 micron.

The silicone copolymer emulsions of the present invention may comprise a silicone copolymer, at least one surfactant, and water.

The silicone copolymer results from the addition reaction of the following two materials in the presence of a metal containing catalyst:

(i) a polysiloxane with reactive groups on both termini, represented by a general formula (IV):

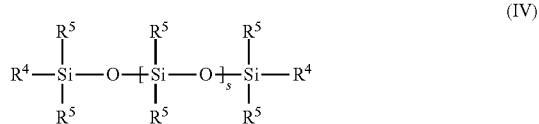
(IV)

wherein:

$R^4$ is a group capable of reacting by chain addition reaction such as, for example, a hydrogen atom, an aliphatic group with ethylenic unsaturation (i.e., vinyl, allyl, or hexenyl), a hydroxyl group, an alkoxyl group (i.e., methoxy, ethoxy, or propoxy), an acetoxyl group, or an amino or alkylamino group;

$R^5$ is alkyl, cycloalkyl, aryl, or alkylaryl and may include additional functional groups such as ethers, hydroxyls, amines, carboxyls, thiols esters, and sulfonates; in an embodiment, $R^5$ is methyl. Optionally, a small mole percentage of the groups may be reactive groups as described above for $R^5$, to produce a polymer which is substantially linear but with a small amount of branching. In this case, the level of $R^5$ groups equivalent to $R^4$ groups may be less than about 10% on a mole percentage basis, such as less than about 2%;

s is an integer having a value such that the polysiloxane of formula (IV) has a viscosity of from about 1 $mm^2s^{-1}$ to about $1\times10^6$ $mm^2s^{-1}$;

and, (ii) at least one silicone compound or non-silicone compound comprising at least one or at most two groups capable of reacting with the $R^4$ groups of the polysiloxane in formula (IV). According to one embodiment, the reactive group is an aliphatic group with ethylenic unsaturation.

The metal containing catalysts used in the above described reactions are often specific to the particular reaction. Such catalysts are known in the art. Generally, they are materials containing metals such as platinum, rhodium, tin, titanium, copper, lead, etc.

The mixture used to form the emulsion also may contain at least one surfactant. This can include non-ionic surfactants, cationic surfactants, anionic surfactants, alkylpolysaccharides, amphoteric surfactants, and the like. The above surfactants can be used individually or in combination.

An exemplary method of making the silicone copolymer emulsions described herein comprises the steps of 1) mixing materials (a) described above with material (b) described above, followed by mixing in an appropriate metal containing catalyst, such that material (b) is capable of reacting with material (a) in the presence of the metal containing catalyst; 2) further mixing in at least one surfactant and water; and 3) emulsifying the mixture. Methods of making such silicone copolymer emulsions are disclosed in U.S. Pat. No. 6,013,682; PCT Application No. WO 01/58986 A1; and European Patent Application No. EP0874017 A2.

A commercially available example of a silicone copolymer emulsion is an emulsion of about 60-70 wt % of divinyldimethicone/dimethicone copolymer having an internal phase viscosity of minimum $120\times10^6$ $mm^2s^{-1}$, available from Dow Corning with a tradename HMW2220.

e. Silicone Polymer Containing Quaternary Groups

The hair conditioner composition may comprise a silicone polymer containing quaternary groups (i.e., a quaternized silicone polymer). The quaternized silicone polymer provides improved conditioning benefits such as smooth feel, reduced friction, prevention of hair damage. Especially, the quaternary group can have good affinity with damaged/colorant hairs. The quaternized silicone polymer is present in an amount of from about 0.1 wt % to about 15 wt %, based on the total weight of the hair conditioning composition. For example, according to an embodiment, the quaternized silicone polymer may be present in an amount from about 0.2 wt % to about 10 wt %, alternatively from about 0.3 wt % to about 5 wt %, and alternatively from about 0.5 wt % to about 4 wt %, by weight of the composition.

The quaternized silicone polymer of the present invention is comprised of at least one silicone block and at least one non-silicone block containing quaternary nitrogen groups, wherein the number of the non-silicone blocks is one greater than the number of the silicone blocks. The silicone polymers correspond to the general structure (V):

(V)

wherein, B is a silicone block having greater than 200 siloxane units; $A^1$ is an end group which may contain quaternary groups; $A^2$ is a non-silicone blocks containing quaternary nitrogen groups; and m is an integer 0 or greater, with the proviso that if m=0 then the $A^1$ group contains quaternary groups.

Structures corresponding to the general formula, for example, are disclosed in U.S. Pat. No. 4,833,225, in U.S. Patent Application Publication No. 2004/0138400, in U.S. Patent Application Publication No. 2004/0048996, and in U.S. Patent Application Publication No. 2008/0292575.

In one embodiment, the silicone polymers can be represented by the following structure (VI)

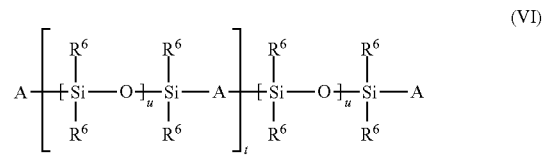
(VI)

wherein, A is a group which contains at least one quaternary nitrogen group, and which is linked to the silicon atoms of the silicone block by a silicon-carbon bond, each A independently can be the same or different; $R^6$ is an alkyl group of from about 1 to about 22 carbon atoms or an aryl group;

each $R^6$ independently can be the same or different; t is an integer having a value of from 0 or greater, for example t can be less than 20, or less than 10; and u is an integer greater than about 200, such as greater than about 250, or greater than about 300, and u may be less than about 700, or less than about 500. According to an embodiment, $R^6$ is methyl.

f. Grafted Silicone Copolyol

The hair conditioner composition may comprise a grafted silicone copolyol in combination with the quaternized silicone polymer. It is believed that this grafted silicone copolyol can improve the spreadability of the quaternized silicone polymer by reducing the viscosity of the quaternized silicone polymer, and also can stabilize the quaternized silicone polymer in aqueous conditioner matrix. It is also believed that, by such improved spreadability, the hair care compositions of the present invention can provide better dry conditioning benefits such as friction reduction and/or prevention of damage with reduced tacky feel. It has been surprisingly found that the combination of the quaternized silicone polymer, grafted silicone copolyol, and cationic surfactant system comprising di-alkyl quaternized ammonium salt cationic surfactants provides improved friction reduction benefit, compared to a similar combination. Such similar combinations are, for example, a combination in which the grafted silicone copolyol is replaced with end-capped silicone copolyol, and another combination in which the cationic surfactant system is substantially free of di-alkyl quaternized ammonium salt cationic surfactants.

The grafted silicone copolyol is contained in the composition at a level such that the weight % of the grafted silicone copolyol to its mixture with quaternized silicone copolymer is in the range of from about 1 wt % to about 50 wt %, alternatively from about 5 wt % to about 40 wt %, and alternatively from about 10 wt % to 30 wt %.

The grafted silicone copolyols useful herein are those having a silicone backbone such as dimethicone backbone and polyoxyalkylene substitutions such as polyethylene oxide and/or polypropylene oxide substitutions. The grafted silicone copolyols useful herein have a hydrophilic-lipophilic balance (HLB) value of from about 5 to about 17, such as from about 8 to about 17, or from about 8 to about 12. The grafted silicone copolyols having the same INCI name have a variety of the weight ratio, depending on the molecular weight of the silicone portion and the number of the polyethylene oxide and/or polypropylene oxide substitutions.

According to an embodiment, exemplary commercially available grafted dimethicone copolyols include, for example: those having a tradename Silsoft 430 having an HLB value of from about 9 to about 12 (INCI name "PEG/PPG-20/23 dimethicone") available from GE; those having a tradename Silsoft 475 having an HLB value of from about 13 to about 17 (INCI name "PEG-23/PPG-6 dimethicone"); those having a tradename Silsoft 880 having an HLB value of from about 13 to about 17 (INCI name "PEG-12 dimethicone"); those having a tradename Silsoft 440 having an HLB value of from about 9 to about 12 (INCI name "PEG-20/PPG-23 dimethicone"); those having a tradename DC5330 (INCI name "PEG-15/PPG-15 dimethicone") available from Dow Corning.

The above quaternized silicone polymer and the grafted silicone copolyol may be mixed and emulsified by a emulsifying surfactant, prior to incorporating them into a gel matrix formed by cationic surfactants and high melting point fatty compounds, as discussed below. It is believed that, this pre-mixture can improve behavior of the quaternized silicone polymer and the grafted silicone copolyol, for example, increase the stability and reduce the viscosity to form more homogenized formulation together with the other components. Such emulsifying surfactant can be used at a level of about 0.001 wt % to about 1.5 wt %, alternatively from about 0.005% to about 1.0%, and alternatively from about 0.01 wt % to about 0.5 wt %, based on the total weight of the hair conditioning composition. Such surfactants may be nonionic, and have an HLB value of from about 2 to about 15, such as from about 3 to about 14, or from about 3 to about 10. Commercially available examples of emulsifying surfactant include nonionic surfactants having an INCI name C12-C14 Pareth-3 and having an HLB value of about 8 supplied from NIKKO Chemicals Co., Ltd. with tradename NIKKOL BT-3.

According to one embodiment, the hair conditioner composition comprises a combination of two or more silicone conditioning agents, along with an EDDS sequestering agent and a gel matrix.

In one embodiment, the hair conditioner composition comprises a polyalkylsiloxane mixture comprising (i) a first polyalkylsiloxane which is non-volatile, substantially free of amino groups, and has a viscosity of from about 100,000 $mm^2s^{-1}$ to about 30,000,000 $mm^2s^{-1}$, and (ii) a second polyalkylsiloxane which is non-volatile, substantially free of amino groups, and has a viscosity of from about 5 $mm^2s^{-1}$ to about 10,000 $mm^2s^{-1}$; an aminosilicone having less than about 0.5 wt % nitrogen by weight of the aminosilicone; and a silicone copolymer emulsion with an internal phase viscosity of greater than about $100 \times 10^6$ $mm^2s^{-1}$, as measured at 25° C. For example, in another embodiment, the hair care composition comprises from about 0.5 wt % to about 10 wt % of a polyalkylsiloxane mixture comprising (i) a first polyalkylsiloxane which is non-volatile, substantially free of amino groups, and has a viscosity of from about 100,000 $mm^2s^{-1}$ to about 30,000,000 $mm^2s^{-1}$, and (ii) a second polyalkylsiloxane which is non-volatile, substantially free of amino groups, and has a viscosity of from about 5 $mm^2s^{-1}$ to about 10,000 $mm^2s^{-1}$; from about 0.1 wt % to about 5 wt % of an aminosilicone having less than about 0.5 wt % nitrogen by weight of the aminosilicone; and from about 0.1 wt % to about 5 wt % of a silicone copolymer emulsion with an internal phase viscosity of greater than about $100 \times 10^6$ $mm^2s^{-1}$, as measured at 25° C.

In another embodiment, the hair conditioner composition comprises a silicone polymer containing quaternary groups wherein said silicone polymer comprises silicone blocks with greater than about 200 siloxane units; and a grafted silicone copolyol. For example, in another embodiment, the hair care composition comprises from about 0.1 wt % to about 15 wt % of a silicone polymer containing quaternary groups wherein said silicone polymer comprises silicone blocks with greater than about 200 siloxane units; and a grafted silicone copolyol at a level such that the weight % of the grafted silicone copolyol in its mixture with the quaternized silicone polymer is in the range of from about 1 wt % to about 50 wt %.

In yet another embodiment, the hair conditioner composition comprises an aminosilicone having a viscosity of from about 1,000 centistokes to about 1,000,000 centistokes, and less than about 0.5% nitrogen by weight of the aminosilicone; and (2) a silicone copolymer emulsion with an internal phase viscosity of greater than about $120 \times 10^6$ centistokes, as measured at 25° C.

2. Other Conditioning Agents

Also suitable for use in the hair conditioner compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422,853.

a. Organic Conditioning Oils

The hair conditioner composition may also further comprise an organic conditioning oil. According to embodiments, the hair conditioner composition may comprise from about 0.05 wt % to about 3 wt %, from about 0.08 wt % to about 1.5 wt %, or even from about 0.1 wt % to about 1 wt %, of at least one organic conditioning oil as the conditioning agent, in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about C12 to about C19. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of C4 to about C14 or even C6 to about C12. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Nonionic Polymers

The hair conditioner composition may also further comprise a nonionic polymer. According to an embodiment, the conditioning agent for use in the hair care composition of the present invention may include a polyalkylene glycol polymer. For example, polyalkylene glycols having a molecular weight of more than about 1000 are useful herein. Useful are those having the following general formula (VIII):

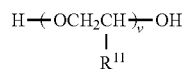

(VIII)

wherein $R^H$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt % to about 10 wt %. In an embodiment, the polyethylene glycol is present in an amount up to about 5 wt % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

4. Suspending Agent

The hair conditioner composition may further comprise a suspending agent at concentrations effective for suspending water-insoluble material in dispersed form in the compositions or for modifying the viscosity of the composition. Such concentrations range from about 0.1 wt % to about 10 wt %, or even from about 0.3 wt % to about 5.0 wt %.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B. F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine Still other suitable suspending agents include di(hydrogenated tallow)phthalic acid amide, and crosslinked maleic anhydride-methyl vinyl ether copolymer.

H. Benefit Agents

The hair conditioner composition can further comprises one or more additional benefit agents. The benefit agents comprise a material selected from the group consisting of anti-dandruff agents, vitamins, lipid soluble vitamins, chelants, perfumes, brighteners, enzymes, sensates, attractants, anti-bacterial agents, dyes, pigments, bleaches, and mixtures thereof.

In one aspect said benefit agent may comprise an anti-dandruff agent. Such anti-dandruff particulate should be physically and chemically compatible with the components of the composition, and should not otherwise unduly impair product stability, aesthetics or performance.

According to an embodiment, the hair conditioner composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active can be included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

Embodiments of the hair conditioner composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the hair conditioner composition comprises an effective amount of a zinc-containing layered material. In an embodiment, the hair conditioner composition comprises from about 0.001 wt % to about 10 wt %, or from about 0.01 wt % to about 7 wt %, or from about 0.1 wt % to about 5 wt % of a zinc-containing layered material, by total weight of the hair conditioner composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2x\ A^-\cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replaces the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

TEST METHODS

The hair conditioner compositions described herein are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair conditioner composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Rinse-off Conditioner and Leave-of Treatment Composition Preparation: The rinse-off conditioner compositions can be prepared by any conventional method well known in the art. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

Shampoo Treatment Protocol

All testing are performed on colored hair switches (see Method of Measurement of copper on hair below) weighing approximately 4.0 grams and having a length of approximately 6 inches. The hair switches are commercially available from IHIP (International Hair Importers). Three hair switches per shampoo composition are used. An amount of 0.20 g of shampoo is spread via a syringe onto separate hair switch. That is, the dosage is 0.10 g of shampoo per g of hair. Each application consists of adding shampoo to the hair, milking for 30 seconds followed by rinsing for 30 seconds. Shampoo is then reapplied (0.1 g/g), milked for 30 seconds and rinsed for 30 seconds. Excess water is squeezed from the hair switches and left to air dry or treated with a rinse-off conditioner and/or a leave-on treatment composition. This protocol is repeated for a number of times/cycles (as indicated in the tables below, which describe the details of hair treatments).

Rinse-off Conditioner Hair Treatment Protocol

All testing are performed on colored hair switches (see Method of Measurement of copper on hair below) weighing approximately 4.0 grams and having a length of approximately 6 inches. The hair switches are commercially available from IHIP (International Hair Importers). Three hair switches per rinse-off compositions are used. Each hair switch is washed with shampoo followed by a treatment with the rinse-off conditioner according to the following protocol.

After treatment with shampoo and after the step of squeezing the excess water from the hair switches (see previous paragraph), 0.1 g/g of the rinse-off conditioner composition is applied and milked for 30 seconds and then rinsed for 30 seconds. This protocol is repeated for a number of times/cycles (as indicated in the tables below.

Leave-on Hair Treatment Protocol

In several cases during this inventigation, the rinse-off conditioner treatment is followed by hair treatment with a leave-on treatment composition. Specifically, the appropriate quantity of the leave-on treatment composition is uniformely sprayed or spread onto separate hair switches (dosage of 0.10 g of solution per g of hair). The hair is then allowed to air dry.

Method of Measurement of Copper on Hair

The following test method was used to assess the ability of the compositions and regimens to remove copper from the hair and to inhibit copper deposition onto the hair.

Hair switches had been colored once with an oxidative hair colorant. An extra blonde shade was used for the testing. The hair switches were washed for 10 or 20 repeat wash cycles in tap water containing 7 grains per gallon water hardness (Ca/Mg) and 0.06 μg/g copper ions. Each wash cycle consisted of two applications of 0.1 g/g a shampoo to the hair switches. Each application consisted of adding shampoo to the hair, milking for 30 secs followed by rinsing for 30 secs. Shampoo was then reapplied 0.1 g/g, milked for 30 secs, rinsed for 30 secs and then dried in a heat box (60° C.) until dry.

Samples of 100 mg of hair were digested overnight with 2 ml of high purity concentrated nitric acid. The digestive mixture also contained 150 μL of 100 μg/g Yttrium internal standard (Inorganic Ventures, Christianburg, Va., USA). Following digestion, samples were heated to 70-80° C. for one hour, cooled to room temperature and diluted to 15 mL with deionized water. Copper content of the hair switches was determined by inductively coupled plasma atomic spectroscopy (ICP-OES)). For each leg, 3 different samples were analyzed.

Similar protocol is utilized for testing regimens, that is, series of products such as shampoo and rinse-off conditioner combinations or shampoo, rinse-off conditioner and/or rinse-off treatment combinations.

Inhibition of copper deposition on hair and facilitation of the removal of copper deposited on hair may also be achieved by applying a leave-on treatment to the hair after rinsing the conditioner from the hair. The leave-on treatment may deliver consumer desired conditioning in addition to inhibiting the deposition of copper (i.e. from the water used to rinse) on the hair. The leave-on treatment described herein may comprise from about 0.025% to about 0.50%, alternatively from about 0.05% to about 0.25% of a chelant selected from Class I, Class II or Class III and mixtures thereof, by weight of the leave-on treatment. The leave-on treatment may also comprise one or more rheology modifiers and an aqueous carrier.

EXAMPLES & DATA

The following are non-limiting examples of the hair conditioner composition described herein. The examples are given solely for the purpose of illustration and are not to be construed as limitations of the hair conditioner composition, as many variations thereof are possible without departing from the spirit and scope of the hair conditioner composition, which would be recognized by one of ordinary skill in the art.

In order to minimize the variability of the variability of the resulting copper content on hair that is related to (a) lot-to-lot variability due to hair switches and (b) day-to-day variability of the water used during shampoo and conditioner treatments, a single lot of hair switches is used for each experimental series and a separate control experiment/treatment is run for each experimental series (see below).

Experimental Series I: Investigation of treatments using shampoos and rinse-off conditioner and leave-on treatments containing 2,3-Triethylenetetramine chelant.
Conditioning shampoo compositions

| Components | Ex. 1 Control Wt % | Ex. 2 Wt % |
| --- | --- | --- |
| Sodium Laureth-3 Sulfate[1] | 6.10 | 6.10 |
| Sodium Lauryl Sulfate[2] | 4.00 | 4.00 |
| Cocoamide MEA[3] | 0.90 | 0.90 |
| Guar hydroxypropyltrimonium chloride[4] | 0.25 | 0.25 |
| Glycol distearate | 1.50 | 1.50 |
| Dimethicone[5] | 1.00 | 1.00 |
| Tetrasodium EDTA dihydrate | 0.16 | 0.16 |
| Citric Acid (Anhydrous) | 0.18 | 0.18 |
| Sodium benzoate | 0.27 | 0.27 |
| Methylchloroisothiazolinone/ Methylisothiazolinone[6] | 0.0006 | 0.0006 |
| Sodium chloride | 0.20 | 0.20 |
| Hydrochloric acid (6N) | 0.06 | 0.06 |
| 2,3-Triethylenetetramine (TETA) | 0.00 | 0.10 |
| Perfume | 0.40 | 0.40 |
| Distilled Water | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Cocamide MEA available from BASF as Comperlan CMEA (85 wt. % active).
[4]Jaguar C-500 available from Ashland.
[5]Silicone oil with viscosity of 330.000 cP
[6]Kathon CG available from Dow (1.5 wt % active).

Clarifying Shampoo Compositions

| Components | Ex. 1(a) Control Wt % | Ex. 3 Wt % |
| --- | --- | --- |
| Sodium Laureth-3 Sulfate[1] | 6.00 | 6.00 |
| Sodium Lauryl Sulfate[2] | 9.50 | 9.50 |
| Cocamidopropyl betaine | 1.88 | 1.88 |
| Tetrasodium EDTA dehydrate | 0.16 | 0.16 |
| Citric Acid (Anhydrous) | 0.28 | 0.28 |
| Sodium benzoate | 0.25 | 0.25 |
| Methylchloroisothiazolinone/ Methylisothiazolinone[3] | 0.0005 | 0.0005 |
| Sodium chloride | 0.57 | 0.57 |
| Hydroxypropylmethylcellulose | 0.25 | 0.25 |
| 2,3-Triethylenetetramine (TETA) | 0.0 | 0.10 |
| Perfume | 0.40 | 0.40 |
| Distilled Water | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Hair Repair Shampoo Compositions

| Components | Ex. 4 Control Wt % | Ex. 5 Wt % |
| --- | --- | --- |
| Ammonium lauryl sulfate | 16.00 | 16.00 |
| Cocoamide MEA[1] | 0.8 | 0.8 |
| Cetyl alcohol | 0.9 | 0.9 |
| Polyquaternium-10[2] | 0.5 | 0.5 |
| Polyethylene glycol 7M[3] | 0.10 | 0.10 |
| Dimethicone[4] | 2.00 | 2.00 |
| Glycol distearate | 1.50 | 1.50 |
| Sodium benzoate | 0.25 | 0.25 |
| Disodium EDTA | 0.13 | 0.13 |
| Citric acid | 0.04 | 0.04 |
| Sodium citrate dehydrate | 0.45 | 0.45 |
| Sodium chloride | 0.03 | 0.03 |
| Methylchloroisothiazolinone/ Methylisothiazolinone[5] | 0.0005 | 0.0005 |

| Components | Ex. 4 Control Wt % | Ex. 5 Wt % |
|---|---|---|
| Perfume | 0.50 | 0.50 |
| 2,3-Triethylenetetramine (TETA) | 0.00 | 0.10 |
| Distilled Water | Q.S. | Q.S. |

[1]Cocamide MEA available from BASF as Comperlan CMEA (85 wt. % active).
[2]Quaternized hydroxyethyl cellulose available from Dow Unival LR30M.
[3]Available by Dow.
[4]Silicone oil with viscosity of 330.000 cP.
[5]Kathon CG available from Dow (1.5 wt % active).

Smoothing Rinse-off Conditioner Compositions

| Components | Ex. 6 Control Wt % | Ex. 7 Wt % |
|---|---|---|
| Stearyl alcohol | 2.32 | 2.32 |
| Cetyl alcohol | 0.93 | 0.93 |
| Dicetyldimonium chloride | 0.34 | 0.34 |
| Behentrimonium methosulfate | 1.16 | 1.16 |
| Propylene glycol | 0.16 | 0.16 |
| Isopropyl alcohol | 0.28 | 0.28 |
| Disodium EDTA Dihydrate | 0.13 | 0.13 |
| Terminal amodimethicone[1] | 0.75 | 0.75 |
| Methylchloroisothiazolinone/Methylisothiazolinone[2] | 0.0005 | 0.0005 |
| Benzyl alcohol | 0.40 | 0.40 |
| 2,3-Triethylenetetramine (TETA) | 0.00 | 0.10 |
| Distilled Water | Q.S. | Q.S. |

[1]Terminal amodimethicone with visc. Of 10,000 cP at 25° C. is available by Momentive Performance Materials.
[2]Kathon CG available from Dow (1.5 wt % active)

Volumizing Rinse-off Conditioner Compositions

| Components | Ex. 7(a) Control Wt % | Ex. 8 Wt % |
|---|---|---|
| Hydroxypropyl guar[1] | 0.35 | 0.35 |
| DTDMAC (Quaternium-18[2]) | 0.75 | 0.75 |
| Stearamidopropyldimethylamine | 1.00 | 1.00 |
| Glyceryl monostearate | 0.25 | 0.25 |
| Emulsifying wax NF (Polywax NF) | 0.50 | 0.50 |
| Cetyl alcohol | 1.20 | 1.20 |
| Stearyl alcohol | 0.80 | 0.80 |
| Oleyl alcohol | 0.25 | 0.25 |
| Citric acid | 0.13 | 0.13 |
| EDTA | 0.10 | 0.10 |
| Terminal amodimethicone[3] | 0.50 | 0.50 |
| 2,3-Triethylenetetramine (TETA) | 0.00 | 0.10 |
| Methylchloroisothiazolinone/Methylisothiazolinone[4] | 0.0005 | 0.0005 |
| Benzyl alcohol | 0.4 | 0.4 |
| Distilled Water | Q.S. | Q.S. |

[1]Jaguar HP-105 supplied by Rhodia
[2]Diatallowdimethylammonium chloride
[3]Terminal amodimethicone with visc. Of 10,000 cP at 25° C. is available by Momentive Performance Materials.
[4]Kathon CG available from Dow (1.5 wt % active).

Hair Repair Rinse-off Conditioner Compositions

| Components | EX. 9 Control Wt % | EX. 10 Wt % |
|---|---|---|
| Behentrimonium chloride | 2.28 | 2.28 |
| Stearyl alcohol | 4.64 | 4.64 |
| Cetyl alcohol | 0.93 | 0.93 |
| Isopropyl alcohol | 0.57 | 0.57 |
| Disodium EDTA Dihydrate | 0.13 | 0.13 |
| Dimethicone[1] | 4.20 | 4.20 |
| Sodium hydroxide | 0.02 | 0.02 |
| Methylchloroisothiazolinone/Methylisothiazolinone[2] | 0.0005 | 0.0005 |
| Benzyl alcohol | 0.40 | 0.40 |
| 2,3-Triethylenetetramine | 0.00 | 0.10 |
| Distilled Water | Q.S. | Q.S. |

[1]Mixture of silicone gum and silicone oil XF49-B1747 available from Momentive Performance Materials.
[2]Kathon CG available from Dow (1.5 wt % active).

Leave-on Treatment Composition

| Components | Ex. 11 Wt % |
|---|---|
| Amodimethicone and Cetrimonium chloride and Trideceth-12[1] | 0.35 |
| Polyquaternium-11[2] | 0.75 |
| PEG-40 Hydrogenated castor oil | 0.50 |
| PPG-2 Methyl ether | 0.5 |
| DMDM Hydantoin | 0.20 |
| Disodium EDTA | 0.14 |
| Poysorbate 80 | 0.12 |
| Aminomethyl propanol | 0.1 |
| Citric acid anhydrous | 0.08 |
| 2,3-Triethylenetetramine | 0.10 |
| Distilled Water | Q.S. |

[1]Siameter MEM-0949 Emulsion available from Dow Corning; it contains 35% amino-silicone
[2]Copolymer of vinylpyrrolidone and quaternized dimethylaminoethyl methacrylate; Gafquat 755 NH available by Ashland Results of Experimental Series I Each treatment (regimen) includes cleaning with conditioning shampoo followed by a rinse-off conditioner, followed by a leave-on treatment spray (when indicated).

| | Ex. 1 Control Conditioning SH (Treatment AM) | Ex. 2 Conditioning SH | Ex. 1 Control Conditioning SH | Ex. 1 Control Conditioning SH |
|---|---|---|---|---|
| Shampoo Composition (SH) | | | | |
| Smoothing Rinse-off conditioner composition (ROC) | Ex. 6 Control Smoothing ROC | Ex. 6 Control Smoothing ROC | Ex. 7 Smoothing ROC | Ex. 6 Control Smoothing ROC |
| Leave-on treatment composition (LOT) | No LOT | No LOT | No LOT | Ex. 11 LOT |
| Summary Description of Composition | SH Control ROC Control No LOT | SH w/chelant ROC Control No LOT | SH Control ROC w/chelant No LOT | SH Control ROC Control LOT w/chelant |

| | | | | |
|---|---|---|---|---|
| Concentration of Chelant | 0% in SH<br>0% in ROC<br>No LOT | 0.1% in SH<br>0% in ROC<br>No LOT | 0% in SH<br>0.1% in ROC<br>No LOT | 0% in SH<br>0% in ROC<br>0.1% in LOT |
| Chelant used | — | 2,3-Triethylene-tetramine | 2,3-Triethylene-tetramine | 2,3-Triethylene tetramine |
| Cycles | 20 | 20 | 20 | 20 |
| Average final copper concentration in hair (ppm) | 84 | 30 | 25 | 43 |
| Standard deviation | 5.6 | 2.1 | 1.7 | 0.2 |
| Relative content of Copper content on hair after treatment (versus control shampoo treatment) | 100 | 36 v. Treatment AM | 30 v. Treatment AM | 51 v. Treatment AM |

| Shampoo Composition (SH) | Ex. 3 Clarifying SH | Ex. 1(a) Control Clarifying SH | Ex. 5 Repair SH | Ex. 4 Control Repair SH |
|---|---|---|---|---|
| Rinse-off conditioner composition (ROC) | Ex. 7(a) Control Volumizing ROC | Ex. 8 Volumizing ROC | Ex. 9 Control Repair ROC | Ex. 10 Repair ROC |
| Leave-on treatment composition (LOT) | No LOT | No LOT | No LOT | No LOT |
| Summary Description of Composition | SH w/chelant ROC Control No LOT | SH Control ROC w/chelant No LOT | SH w/chelant ROC Control No LOT | SH Control ROC w/chelant No LOT |
| Concentration of Chelant | 0.1% in SH<br>0% in ROC<br>No LOT | 0% in SH<br>0.1% in ROC<br>No LOT | 0.1% in SH<br>0% in ROC<br>No LOT | 0.1% in SH<br>0% in ROC<br>No LOT |
| Chelant used | — | 2,3-Triethylene-tetramine | 2,3-Triethylene-tetramine | 2,3-Triethylene-tetramine |
| Cycles | 20 | 20 | 20 | 20 |
| Average final copper concentration in hair (ppm) | 32 | 28 | 35 | 26 |
| Standard deviation | 1.6 | 3.4 | 4.5 | 0.7 |
| Relative content of Copper content on hair after treatment (versus control shampoo treatment) | 35 v. Treatment AM | 30 v. Treatment AM | 38 v. Treatment AM | 28 v. Treatment AM |

Addition of 2,3-Triethylenetetramine in any of the products of the regimen contributes to an effective removal of copper from hair after 20 conditioning shampoo/rinse-off conditioner/leave-on treatment regimen cycles compared to the corresponding treatment with control conditioning shampoo/control rinse-off conditioner. The regimen where the chelant is added in the leave-on treatment is particulary effective in removing copper form hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the hair conditioner composition have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method comprising:
   a. inhibiting copper deposition on hair and facilitating the removal of copper deposited on hair by applying to the hair a conditioner composition comprising:
      i. from about 0.1% to about 1.5%, by weight of the composition, of a chelant wherein the chelant consists of 2,3-Triethylenetetramine;
      ii. a gel matrix comprising:
         1. from about 1% to about 8%, by weight of the composition, of a fatty alcohol selected from the group consisting of cetyl alcohol, stearyl alcohol, behenyl alcohol, and combinations thereof;
         2. from about 0.8% to about 5%, by weight of the composition, of a cationic surfactant; and
         3. an aqueous carrier;
      iii. a pH from about 3 to about 8;
   wherein the chelant penetrates inside a hair fiber to form a copper-chelant complex;
   wherein the copper-chelant complex is water-soluble;

b. rinsing the hair conditioner composition and the copper-chelant complex from the hair thereby removing the copper from the hair.

2. The method of claim 1, wherein the conditioner composition further comprises from about 0.1% to about 5%, by weight of the composition, of a silicone.

3. A method comprising:
 a. inhibiting copper deposition on hair and facilitating the removal of copper deposited on hair by applying to the hair a conditioner composition comprising:
  i. from about 0.005% to about 5% of a chelant, by weight of the hair conditioner composition, wherein the chelant has a molecular structure as follows:

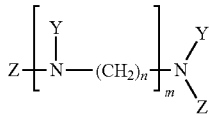

wherein n is 2 or 3; m is 1, 2, 3, or 4; and
Y and Z are independently selected from the group consisting of hydrogen, methyl, ethyl, propyl, butyl, pentyl, —CH$_2$CH$_2$OH, —CH$_2$CH(CH$_3$)OH), —CH$_2$CH$_2$NH$_2$, —CH$_2$CH(CH$_3$) NH$_2$, and combinations thereof;
and wherein the one or more chelants comprise:
  1. log of the formation constant logK$_{ML}$ of its complex with copper is higher than 6;
  2. log P value is from about −5 to about 2; and
  3. molecular weight of from about 50 to about 500;
 ii. a gel matrix comprising:
  1. from about 0.1% to about 20% of a high melting point fatty compounds, by weight of the hair conditioner composition;
  2. from about 0.1% to about 10% of a cationic surfactant, by weight of the hair conditioner composition; and
  3. an aqueous carrier;
 iii. a pH from about 3 to about 8;
wherein the chelant penetrates inside a hair fiber to form a copper-chelant complex;
wherein the copper-chelant complex is water-soluble;
b. rinsing the hair conditioner composition and the copper-chelant complex from the hair thereby removing the copper from the hair.

4. The method of claim 3, wherein the hair conditioner composition further comprises silicone.

5. The method of claim 3, wherein the hair conditioner composition further comprises one or more benefit agents.

6. The method of claim 4, wherein the one or more benefit agents is selected from the group consisting of anti-dandruff agents, vitamins, perfumes, brighteners, enzymes, sensates, attractants, anti-bacterial agents, dyes, pigments, bleaches, and mixtures thereof.

7. The method of claim 3, wherein the cationic surfactant comprises at least one alkyl group with a carbon chain comprising at least 22 carbon atoms.

8. The method of claim 3, wherein the chelant is selected from the group consisting of 2,3-triethylenetetramine, tetraethylenepentamine, 2,4-tetraethylenepentamine, pentaethylenehexamine, tris(2-aminoethyl)amine, ethylenedinitrilotetrapropan-2-ol, 1, 1',1", 1'''R2-hydroxypropylliminolbis (2,1ethanediylnitrilo) tetrakis-2-prop anol, tetraethylenepentaamine-(1-EO), 1,5,9,13-Tetraazatridecane, and mixtures thereof.

9. The method of claim 3, wherein the log P value of the chelant is from about −4 to about 1.

10. The method of claim 3, wherein the log P value of the chelant is from about −3 to about 0.

11. The method of claim 3, wherein the molecular weight of the chelant is from about 75 to about 400.

12. The method of claim 3, wherein the molecular weight of the chelant is from about 100 to about 350.

13. The method of claim 3, wherein the molecular weight of the chelant is from about 125 to about 325.

14. The method of claim 3, wherein the molecular weight of the chelant is from about 140 to about 300.

15. The method of claim 3, wherein the hair conditioner composition comprises from about 0.01% to about 3% of the chelant.

16. The method of claim 3, wherein the hair conditioner composition comprises from about 0.01% to about 1% of the chelant.

17. The method of claim 3, wherein the hair conditioner composition comprises from about 0.01% to about 0.5% of the chelant.

18. The method of claim 3, wherein the hair conditioner composition comprises from about 0.01% to about 0.1% of the chelant.

19. The method of claim 3, wherein the hair conditioner composition comprises from about 0.025% to about 0.05% of the chelant.

* * * * *